United States Patent
Hansen

(10) Patent No.: US 7,635,451 B2
(45) Date of Patent: Dec. 22, 2009

(54) APPARATUS AND METHOD FOR PASTEURIZING PRODUCTS

(75) Inventor: Lars Hendrik Hansen, Brondby (DK)

(73) Assignee: Sander Hansen A/S, Brondby (DK)

( * ) Notice: Subject to any disclaimer, the term of this patent is extended or adjusted under 35 U.S.C. 154(b) by 593 days.

(21) Appl. No.: 10/787,790

(22) Filed: Feb. 26, 2004

(65) Prior Publication Data

US 2005/0003064 A1 Jan. 6, 2005

(30) Foreign Application Priority Data

Mar. 7, 2003 (DE) ................................. 103 10 047

(51) Int. Cl.
*A23L 3/00* (2006.01)
*A61L 2/18* (2006.01)

(52) U.S. Cl. ............................... 422/26; 422/1; 422/38; 700/266; 700/282; 99/453; 99/468; 99/483; 426/231; 426/233; 426/407; 426/521

(58) Field of Classification Search ................. 700/274; 426/521, 522, 580
See application file for complete search history.

(56) References Cited

U.S. PATENT DOCUMENTS

| | | | | |
|---|---|---|---|---|
| 4,639,854 A | * | 1/1987 | Kurokawa et al. | 700/37 |
| 4,912,386 A | * | 3/1990 | Lurie | 318/615 |
| 5,115,418 A | * | 5/1992 | Shimada | 318/616 |
| 5,360,594 A | * | 11/1994 | Meijer | 422/37 |
| 6,424,873 B1 | * | 7/2002 | Przybylski | 700/42 |
| 2003/0049356 A1 | * | 3/2003 | Nielsen et al. | 426/522 |

FOREIGN PATENT DOCUMENTS

| | | | |
|---|---|---|---|
| CA | 1080830 | * | 7/1980 |
| DE | 3637661 A1 | | 5/1997 |
| EP | 0586763 A2 | | 3/1994 |
| EP | 1454540 | * | 9/2004 |

* cited by examiner

*Primary Examiner*—P. Kathryn Wright
(74) *Attorney, Agent, or Firm*—Marshall, Gerstein & Borun LLP

(57) ABSTRACT

Apparatus and method for pasteurizing products, in particular filled receptacles, such as bottles. The apparatus is provided with a control unit having a first control circuit that is controlled according to a first criterion. At least one second control circuit, controlled according to a second criterion, is also provided. The second control circuit is superimposed on the first control circuit.

9 Claims, 2 Drawing Sheets

APPARATUS AND METHOD FOR PASTEURIZING PRODUCTS

FIELD OF THE INVENTION

The invention relates to an apparatus and method for pasteurizing products, in particular filled receptacles, such as bottles and cans, and to such an apparatus provided with a control unit comprising a first control circuit which is adapted to be controlled according to a first criterion.

BACKGROUND OF THE INVENTION

In conventional heat-treatment plants, especially in plants used for pasteurizing products, control is effected according to the number of pasteurization units transferred (PU control). The pasteurization units, which are abbreviated hereinbelow with PU, are calculated according to the following formula:

$$\frac{dPU}{dt} = 10^{\left[\frac{t_p - T_{ref}}{z}\right]}$$

In this formula, $T_p$ stands for the product temperature, the pasteurization parameters being normally $T_{ref}$=60° C. and z=6.949468.

Depending on the product in question, a certain pasteurization degree is determined, which is necessary for achieving a sufficient preservation of the product, without impairing it. According to this pasteurization degree, the pasteurization units to be absorbed by the respective product are determined; the transfer of these pasteurization units must be guaranteed by a suitable temperature control of the plant in question.

An apparatus for pasteurizing products, which is manufactured by the applicant, is known from European patent 0 437 499 B1. By means of this known apparatus, excessive or insufficient pasteurization of the products is avoided, when the plant is stopped during the heat treatment, and the power consumed is reduced simultaneously. In the known apparatus, this is achieved by crosswise rerouting spray liquids, which flow off from zones with different temperatures, in such a way that cooler products in a pasteurization area are used for cooling warmer products at a different location in said apparatus by means of heat compensation of the spray liquid in this area. An additional supply of cold spray liquid or a discharge of warm spray liquid and the resultant power losses are avoided in this way.

This known apparatus is controlled exclusively according to the number of pasteurization units transferred, which must reach a specific reference value, i.e. a specific pasteurization degree within close tolerances.

DE 36 37 661 C2 discloses a method for pasteurizing products, with the aid of which a power-saving and reliable pasteurization is to be made possible even if malfunctions occur when the receptacles to be pasteurized pass through the plant. In order to achieve this, a prepasteurization zone and a pasteurization zone are subdivided into controllable elementary zones; in each elementary zone, at least one reference receptacle is observed and the number of pasteurization units absorbed by said receptacle is calculated. When a specific reference value is exceeded or not reached, cooling or heating of the respective zone is initiated, whereby an optimum, variable adaptation of the spray temperature can be effected, when the speed of passage is known.

Also in the case of this known method, process control is effected exclusively in accordance with the number of pasteurization units transferred.

An apparatus of the type mentioned at the beginning is produced and marketed by the applicant.

Just as the above-described plant and the above-described method, the control unit of this known apparatus supports process control according to a reference value of a controlled variable, in particular according to a reference value of the pasteurization units.

In addition, the known apparatus also permits one or a plurality of other criteria to be supervised, e.g. the lethal temperature, i.e. the temperature that has to be reached for killing germs. On the basis of the result of this supervision, a heat treatment is carried out after the normal pasteurization process, if necessary, e.g. if a product does not reach a certain temperature level, i.e. the germ-killing point, prior to leaving the last heat treatment zone. A conveyor belt transporting the product in question is then stopped and the thermal aftertreatment is carried out until the supervised criterion has been fulfilled; this results in considerable downtimes of the plant.

This intervention in the process sequence is a control, i.e. there is no closed signal circuit in which a controlled output magnitude acts back on a controlling input magnitude. In contrast to a closed-loop control, an open process, which does not comprise an adaptation of an actual magnitude to a reference magnitude, takes place in the known apparatus.

Known pasteurization plants have, on the whole, only been controlled according to a single reference criterion up to now; this criterion is normally the pasteurization degree. It is also known to supervise, in addition to the pasteurization unit control, other criteria, e.g. the killing-point temperature; the supervision result is, however, not incorporated in the control, but is only used for carrying out a subsequent heat treatment, if necessary.

It follows that, if a criterion other than the control criterion is not fulfilled in the sequence of normal pasteurization steps carried out in the case of the known control processes, an aftertreatment has to be carried out until the respective criterion is fulfilled. This results in undesired downtimes of the plant.

SUMMARY OF THE INVENTION

It is therefore the object of the present invention to provide a pasteurization apparatus and a pasteurization method which allow comparatively long downtimes to be avoided, even if a criterion other than the control criterion is not fulfilled.

The invention provides the advantage that a plurality of different criteria are taken into account simultaneously in the control, whereby the quality of the control is improved. By taking into account a plurality of criteria simultaneously, the pasteurization reliability is increased as well, since various reliability aspects, e.g. a certain lethal temperature that has to be reached, are thus incorporated in the control process.

In addition, when it is foreseeable that a further criterion is not fulfilled, the temperature is readjusted during the sequence of normal process steps in the apparatus according to the present invention. In this way, downtimes are reduced in comparison with a known apparatus which is close-loop controlled according to only one criterion and which only supervises other criteria and uses them for open-loop control.

Preferably, the second control circuit is linked to the first control circuit at a mixing point, which is adapted to have supplied thereto an input signal that corresponds to a reference value of the first criterion, and an output signal of the second control circuit. The output signal of the second control circuit modulates the input signal of the first control circuit. This embodiment of the apparatus according to the present invention realizes in a simple manner the superposition of the second control circuit on the first control circuit, the reference value of the first criterion being influenced by the fact that the input signal of the first control circuit is modulated by the output signal of the second control circuit. This has the effect that the control according to the second criterion of the second control circuit is incorporated in the first control circuit.

According to a preferred embodiment of the present invention, the first control circuit comprises a comparator arranged subsequent to the mixing point, said comparator comparing the input signal modulated in the mixing point and a further signal corresponding to an actual value of the first criterion, and outputting an output signal which corresponds to a control deviation resulting from the reference value/actual value comparison. The input signal of the first control circuit, which has been modulated in the mixing point by the output signal of the second control circuit, is in this way used as a reference magnitude to which the actual value of the first criterion is adapted.

According to another preferred embodiment of the apparatus according to the present invention, the comparator is followed by at least one controller and one actuator, the output signal of the comparator, which corresponds to the control deviation, being adapted to be supplied to the controller.

The second control circuit preferably includes a comparator which compares an input signal corresponding to a reference value of the second criterion and a further signal corresponding to an actual value of the second criterion. The comparator outputs an output signal corresponding to a control deviation resulting from the reference value/actual value comparison. On the basis of this reference value/actual value comparison, the second control criterion is incorporated in the second control circuit in an advantageous manner, whereby it will be possible to use, on the basis of the superposition of the second control circuit on the first control circuit, said second control criterion for modulating the input signal of the first control circuit.

According to another advantageous embodiment of the apparatus according to the present invention, the comparator of the second control circuit is followed by a controller, the output signal of the comparator of the second control circuit, which corresponds to the control deviation, being adapted to be supplied to this controller which outputs the output signal that is adapted to be supplied to the mixing point for modulating the input signal of the first control circuit. The controller of the second circuit adapts in an advantageous manner the actual value of the second criterion to the reference value of the second control criterion inputted in the comparator.

Another advantageous embodiment of the apparatus according to the present invention is so conceived that the first and the second control circuit each comprise a unit for calculating the actual values of the respective criteria form a process parameter, in particular the spray temperature. The advantage of this embodiment of the present invention is to be seen in the fact that, on the basis of a single process parameter, in particular the spray temperature, different control criteria or rather the actual values of these control criteria are calculated so that, on the basis of the determination of various criteria, various aspects of the sequence of process steps can be taken into account in the control.

Preferably, the first criterion comprises pasteurization units and the second criterion a different magnitude, such as a lethal temperature. This has the advantageous effect that, when the second control circuit, which is controlled in accordance with the lethal temperature, is superimposed on the first control circuit, which is controlled in accordance with pasteurization units, it will be guaranteed that a sufficient pasteurization degree will be observed on the one hand, and that the temperature during the pasteurization process will neither fall below nor fail to reach the lethal temperature on the other, whereby the reliability of the process, i.e. a reliable killing of germs, will be improved. When a different magnitude is selected for the second criterion, respective other focal points can be incorporated into the control, i.e. it is important that the first and the second criterion are different so as to be able to take into account various control aspects.

According to a further advantageous embodiment of the apparatus according to the present invention, additional control circuits can be provided, which are each adapted to be controlled according to further criteria, the output signals of said additional control circuits being adapted to be supplied to the mixing point and influencing the input signal of the first control circuit. On the basis of this extended version of the control unit, an even more complex and more comprehensive control of the sequence of process steps is possible, in the case of which further criteria are additionally taken into account and incorporated in the control.

The additional control circuits can each comprise a mixing point at which each additional control circuit is linked to the respective preceding control circuit. In this way, the output signal of the respective preceding control circuit is modulated by the output signal of the additional control circuit so that the modulated output signal can be transmitted to the mixing point of the first control circuit, whereby the input signal of the first control circuit will be influenced by the modulated total output signal of the additional control circuits.

BRIEF DESCRIPTION OF THE DRAWINGS

In the following, the present invention will be explained on the basis of schematic drawings exemplarily and with regard to further details.

DETAILED DESCRIPTION OF THE INVENTION

Figure 1:
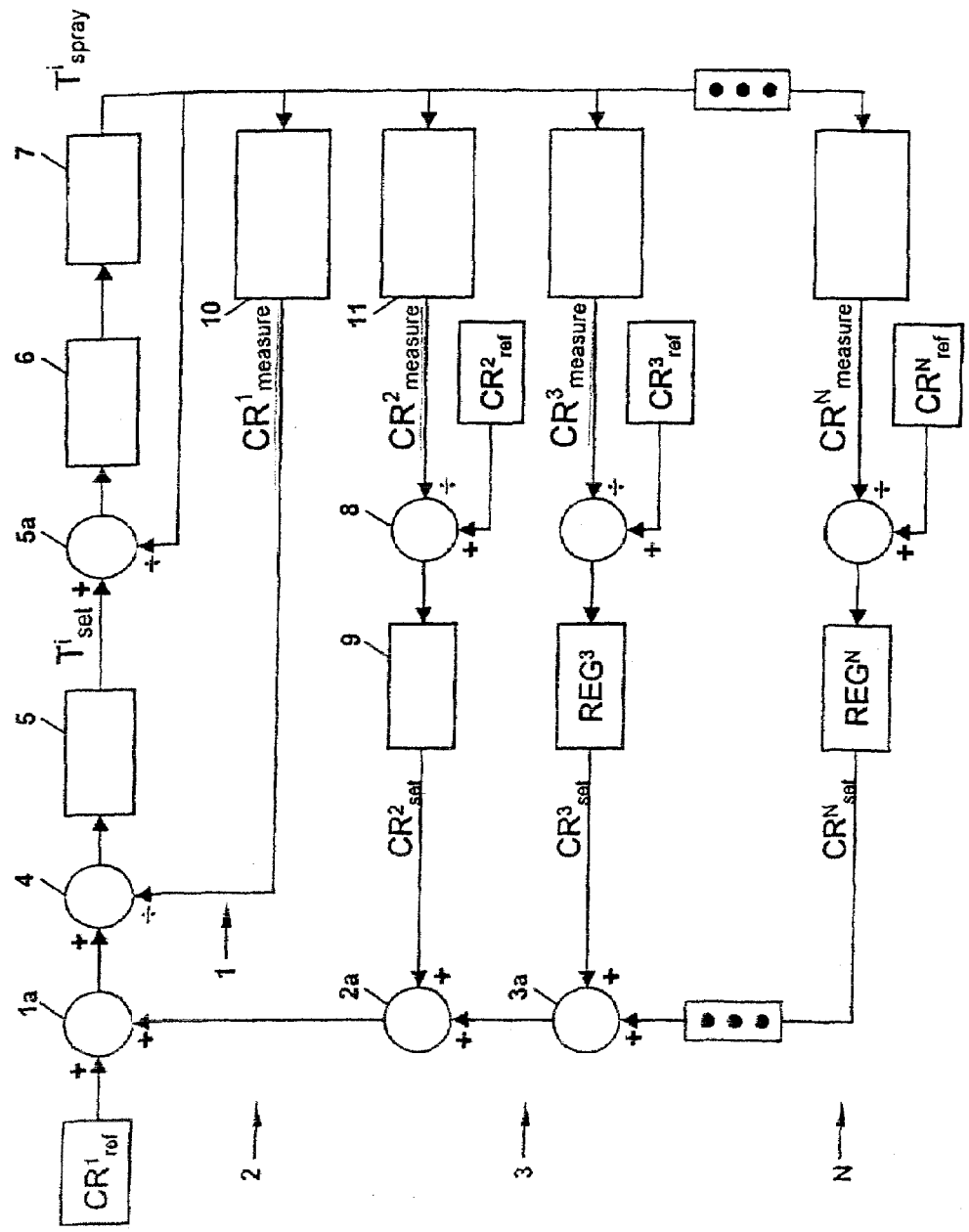
FIG. 1 shows a block diagram with the signal flow of an embodiment of a closed-loop control of the apparatus according to the present invention for N control circuits.

FIG. 1 shows in the form of a block diagram the control of an embodiment of the apparatus according to the present invention. This control is executed by a closed-loop control unit which may comprise a measuring probe, a measuring transducer, a measuring amplifier, a set point generator, a comparator, a controller, a motor, an actuator as well as other components of which only the comparator, the controller and the actuator are shown in FIG. 1.

It goes without saying that the invention is not limited to the components of the control unit shown in FIG. 1, but it also comprises the above-mentioned additional components of the control unit.

As can be seen in FIG. 1, the first closed-loop control circuit 1 has superimposed thereon at least one second closed-loop control circuit 2; as can also be seen in FIG. 1, the first control circuit 1 has additionally superimposed thereon further control circuits 3 to N.

The first circuit 1 has the following composition:

according to the logic diagram of the first control circuit shown in FIG. 1, an input signal $CR^1_{ref}$, which corresponds to a reference value of the first control criterion, is supplied via a mixing point 1a to a comparator 4, which compares the input signal $CR^1_{ref}$ with a further signal $CR^1_{measure}$ that corresponds to an actual value of the first criterion. The comparator 4 determines a control deviation between the reference value and the actual value of the first criterion and outputs an output signal which is not identified in detail in FIG. 1 and which corresponds to this control deviation. This output signal of the comparator 4 is supplied to a controller 5 of the first control circuit 1. Said controller 5 can e.g. by a PI controller or a PID controller.

The controller 5 outputs a specific spray water temperature $T^i_{set}$ as an actuating variable which is supplied to a further comparator 5a of the first control circuit 1. In this further comparator 5a, the spray temperature outputted by the controller 5 is compared with the actual spray temperature $T^i_{spray}$, the comparator 5a outputting an output signal, which corresponds to a control deviation between the spray temperature $T^i_{spray}$ and which is not specified in FIG. 1 either.

The comparator 5a of the first control circuit 1 is followed by a follow-up controller 6, e.g. a PID controller, which applies to a motor a respective actuating signal, said motor being not shown in FIG. 1. This motor drives an actuator 7, e.g. a valve, which controls the spray temperature $T^i_{spray}$ in the pasteurization plant.

As has been explained hereinbefore, the actual spray temperature $T^i_{spray}$ is fed back in the comparator 5a. Due to the series connection of the controller 5 and of the follow-up controller 6 of the first control circuit 1, a cascade control is obtained, which improves the quality of the first control circuit.

The feedback of the spray temperature $T^i_{spray}$, an actual value of the first criterion is calculated from said actual spray temperature $T^i_{spray}$ in the unit 10 and outputted as the signal $CR^1_{measure}$.

In addition to the feedback of the actual spray temperature $T^i_{spray}$, an actual value of the first criterion is calculated from said actual spray temperature $T^i_{spray}$ in the unit 10 and outputted as the signal $CR^1_{measure}$.

As will be explained in connection with the description of FIG. 2, the unit 10 determines, with the aid of a computer-assisted computational model, the pasteurization units absorbed by a receptacle in the pasteurization plant, on the basis of the predetermined spray temperatures $T^i_{spray}$ of the respective zones. The product that has absorbed the lowest number of pasteurization units is selected as reference product, the pasteurization degree of this product corresponding to the actual value of the first criterion, i.e. to the transferred pasteurization units. The signal $CR^1_{measure}$ is fed back via the comparator 4, which, on the basis of the input signal $CR^1_{ref}$ corresponding to the reference value of the first criterion, i.e. to the aimed-at pasteurization degree, outputs a certain control deviation.

It goes without saying that the invention is not limited to a version in which the determination of the pasteurization units absorbed serves as first criterion. Other criteria, such as the determination of oxidation units or thermal decomposition units, can be used as a first criterion as well.

The second control circuit 2, which is superimposed on the first control circuit 1, comprises a comparator 8 of the type shown in FIG. 1. This comparator 8 of the second control circuit 2 has supplied thereto an input signal $CR^2_{ref}$ which corresponds to a reference value of the second control criterion. Furthermore, the comparator 8 of the second control circuit 2 has supplied thereto an additional signal $CR^2_{measure}$ corresponding to an actual value of the second control criterion.

On the basis of these two signals $CR^2_{ref}$ and signal $CR^2_{measure}$ a control deviation is formed in the comparator 8 of the second control circuit 2, said control deviation being transmitted to the controller 9 of the second control circuit 2. In said controller 9, the actual value is adapted to the reference value of the second criterion, an output signal $CR^2_{ref}$ being outputted by the controller 9 of the second control circuit 2 as an actuating variable.

This output signal $CR^2_{set}$, which is representative of the control deviation between the reference value and the actual value of the second control criterion, is fed into the first control circuit at the mixing point 1a. It follows that the input signal $CR^1_{ref}$ of the first control circuit is modulated by the output signal $CR^2_{set}$ of the second control circuit in the mixing point 1a, so that the control of the second criterion, which has taken place in the second control circuit 2, will be introduced into the control of the first control circuit 1.

If, as will be explained in connection with FIG. 2, the first control circuit 1 is controlled e.g. according to the number of pasteurization units absorbed and if the second control circuit 2 is controlled according to the lethal temperature, the reference value of the pasteurization units will, for example, be increased by the output signal $CR^2_{set}$ of the controller 9 of the second control circuit 2, if it is ascertained in the comparator 8 of the second control circuit that the lethal temperature set is not achieved.

As can additionally be seen in FIG. 1, the spray temperature $T^i_{spray}$ represents the basis for calculating the actual value of the first criterion and the actual value of the second criterion. The calculation of the two actual values takes place in the units 10, 11 with the aid of a computer-assisted computational model, the unit 10 calculating e.g. the number of pasteurization units absorbed by the product in the pasteurization plant and the unit 11 calculating e.g. the lethal temperature prevailing in the product. The calculation of the respective control criteria. i.e., for example, the number of pasteurization units transmitted, is carried out in a manner known per se and is therefore no longer explained here.

The additional control circuits 3 to N can be constructed like the second control circuit 2 and they process a control deviation of a further control criterion, which also results from the spray temperature through the application of a computational model.

The output signals $CR^3_{set}$ to $CR^N_{set}$ of the further control circuits are supplied indirectly to the mixing point 1 a of the first control circuit 1 and influence in this way the input signal $CR^1_{ref}$. The indirect supply of the respective output signals $CR^3_{set}$ to $CR^N_{set}$ to the mixing point 1a is effected via additional mixing points 2a to Na. These additional mixing points 2a to Na connect a respective preceding control circuit to a subsequent control circuit. This means that the output signal of the subsequent control circuit modulates the output signal of the preceding control circuit at the mixing point of the preceding control circuit, the modulated output signal of the preceding control circuit being supplied to the mixing point 1a and, respectively, the mixing point of another control circuit which is a preceding control circuit as well.

It is, of course, also possible to provide a different type of supply of the output signals $CR^3_{set}$ to $CR^N_{set}$ to the mixing point 1a of the first control circuit. It is also imaginable to supply the respective output signals $CR^3_{set}$ to $CR^N_{set}$ of the additional control circuits 3 to N directly to the mixing point 1a of the first control circuit 1. A combination of direct and indirect supply of the respective output signals can be used as well. The provision of a plurality of mixing points instead of one mixing point 1a of the first control circuit 1 is also possible for modulating the input signal $CR^1_{ref}$ with the aid of the respective output signals of the additional control circuits.

In the following, another embodiment of the apparatus according to the present invention will be explained making reference to FIG. 2, said embodiment comprising a control unit with two control circuits.

Figure 2:
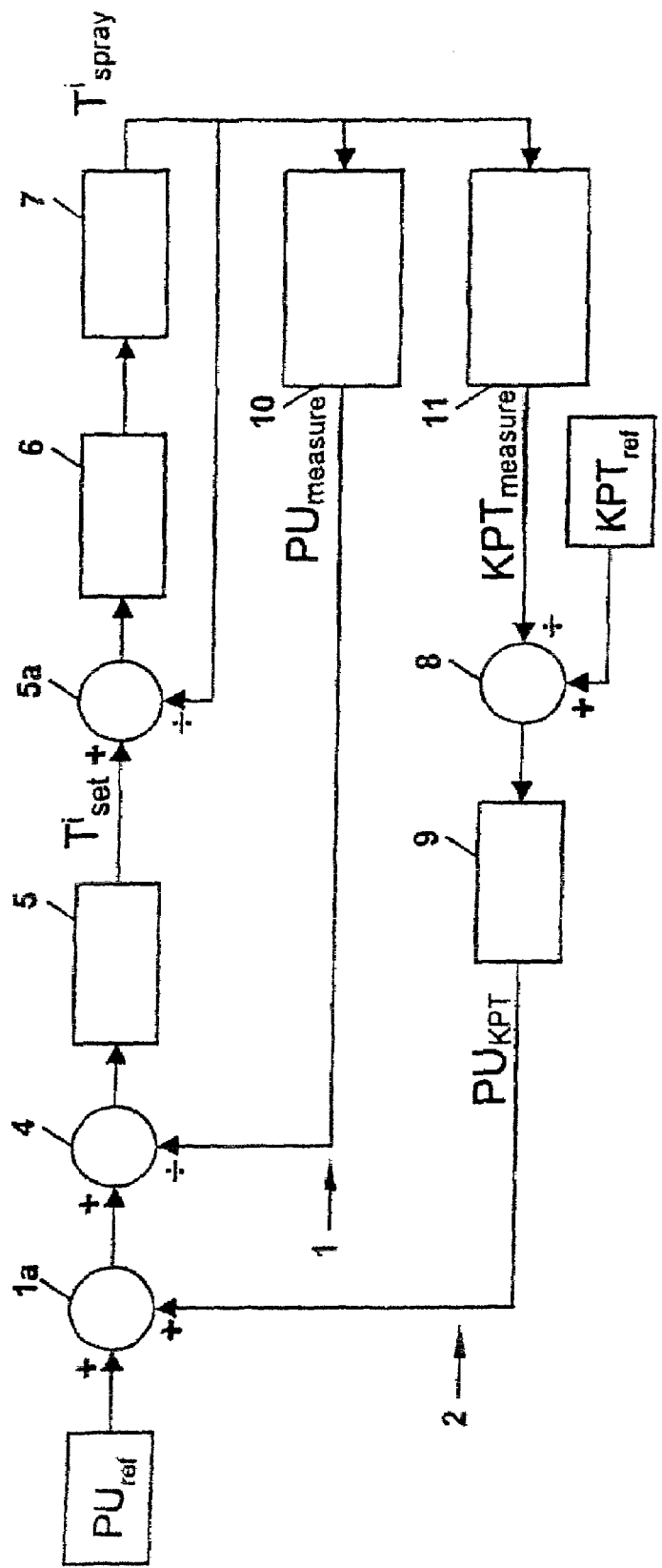
FIG. 2 shows a block diagram with the signal flow of an embodiment of a closed-loop control of the apparatus according to the present invention with two concretely implemented control circuits.

The control unit shown in FIG. 2 comprises a first control circuit 1 and a second control circuit 2 which is superimposed on said first control circuit 1. The first control circuit 1 comprises the comparator 4, which is followed by the controller 5, k e.g. a PI controller or a PID controller. A further comparator 5a is provided between the controller 5 and the follow-up controller 6, which is e.g. a PID controller. The follow-up controller 6 is followed by the actuator 7, e.g. a valve. The feedback of the first control circuit 1 is effected, on the one hand, via the comparator 5a which is arranged between the controller 5 and the follow-up controller 6. In the comparator 5a the actual spray temperature $T^i_{spray}$ is fed back.

On the basis of said spray temperature $T^i_{spray}$, the pasteurization units actually absorbed by the products or by a reference product are calculated in the unit 10 with the aid of a suitable model. The unit 10 for calculating the actual value of the pasteurization units outputs a signal $PU_{measure}$ which is fed back in the comparator 4.

The comparator 4 compares the output signal $PU_{measure}$ i.e. the pasteurization units actually absorbed, with the input signal $PU_{ref}$ of the first control circuit 1, which corresponds to the actual value of the pasteurization units. The control deviation between the actual value and the reference value of the pasteurization units, which is ascertained in the comparator 4, is fed into the controller 5 which outputs a specific spray temperature $T^i_{set}$ as actuating temperature that is inputted in the comparator 5a. The actual spray temperature $T^i_{spray}$ is fed back into this spray temperature, the follow-up controller 6 applying to the motor of the actuator 7a respective actuating signal on the basis of this feedback. The actuator 7 will then influence the spray temperature $T^i_{spray}$ in the respective zones of the pasteurization plant.

Also in this example, the cascade control, which comprises the controller 5, the comparator 5a and the follow-up controller 6, is subordinated to the first control circuit 1 and serves to improve the control quality still further.

The second control circuit 2 comprises a controller 9, a comparator 8 preceding said controller 9, and a unit 11 for calculating the actual value of the second criterion. A reference value of the lethal temperature is fed as input signal $KPT_{ref}$ into the comparator 8 where it is compared with an actual value of the lethal temperature, i.e. an output signal of the unit for calculating the actual value of the lethal temperature. The control deviation obtained in said comparator 8 is inputted into the controller 9 which supervises this so-called local criterion.

The controller 9 outputs a signal $PU_{KPT}$ as an actuating variable, which is supplied to the mixing point 1a. Depending on whether the actual product temperature is lower or higher than the lethal temperature, a circumstance ascertained in the comparator 8, the output signal $PU_{KPT}$ of the controller 9 of the second control circuit 2 influences the input signal $PU_{ref}$ of the first control circuit 1. If, for example, the reference value of the lethal temperature is not reached in the receptacles in the pasteurization plant, the number of pasteurization units of the reference value $PU_{ref}$ will be increased by the output signal $PU_{KPT}$. This has the effect that the pasteurization units will be adapted to the lethal temperature.

With the aid of the present embodiment of the apparatus according to the present invention, control is effected not only according to the number of pasteurization units absorbed but also according to the lethal temperature. In this way, it is avoided that an additional heat treatment has to be carried out after the normal passage through the pasteurization plant, if a criterion other than the number of transferred pasteurization units, e.g. the lethal temperature, is not fulfilled. In the embodiment of FIG. 2, the number of transferred pasteurization units as well as the lethal temperature are simultaneously taken into account in the control so that possible downtimes of the pasteurization plant caused by subsequent heat treatments are suppressed.

The invention claimed is:

1. An apparatus for pasteurizing filled receptacles, comprising a control unit comprising a first control circuit (1) which is adapted to be controlled according to a first criterion, and at least one second control circuit (2) which is adapted to be controlled according to a second criterion, and the second control circuit (2) being superimposed on the first control circuit (1), wherein the first and the second control circuit (1, 2) each comprise a unit (10, 11) for calculating the actual values of the respective first and second criteria from a single and same process parameter, wherein the second control circuit (2) is linked to mixing point (1a), which is adapted to have supplied thereto an input signal $CR^1_{ref}$ of the first control circuit (1) that corresponds to a reference value of the first criterion, and an output signal $CR^2_{set}$ of the second control circuit (2), the output signal $CR^2_{set}$ of the second control circuit (2) modulating the input signal $CR^1_{ref}$ of the first control circuit (1), wherein the mixing point (1a) is located in an input branch of the first control circuit (1), further comprising additional control circuits (3, ... N), which are each adapted to be controlled according to further criteria, output signals $CR^3_{set}$ ... $CR^N_{set}$ of the additional control circuits (3, ... N) being adapted to be supplied to the mixing point (1a) and influencing the input signal $CR^1_{ref}$ of the first control circuit (1), wherein the additional control circuits (3, ... N) each comprise a mixing point (3a ... Na) at which each additional control circuit is linked to the respective preceding control circuit, wherein the additional control circuits (3, ... N) each comprise a unit for calculating actual values of the respective $3^{rd}$ to $N^{th}$ criteria from the single and same process parameter, wherein the first criterion comprises pasteurization units PU and the second criterion comprises a criterion different from the first criterion, and wherein the single and same process parameter is a spray temperature $T^i_{spray}$, which transfers the pasteurization units PU to the filled receptacles.

2. An apparatus according to claim 1, wherein the first control circuit (1) comprises a comparator (4) arranged subsequent to the mixing point (1a), the comparator (4) comparing the input signal $CR^1_{ref}$ modulated in the mixing point (1a) and a further signal $CR^1_{measure}$ corresponding to an actual value of the first criterion, and the comparator outputting an output signal which corresponds to a control deviation resulting from the reference value/actual value comparison.

3. An apparatus according to claim 1, wherein the comparator (4) is followed by at least one controller (5, 6) and one actuator (7), and the output signal of the comparator (4), which corresponds to the control deviation, being adapted to be supplied to the controller (5, 6).

4. An apparatus according to claim 1, wherein the second control circuit (2) comprises a comparator (8) that is followed by a controller (9), wherein an output signal of the comparator (8) of the second control circuit (2), which corresponds to the control deviation, is adapted to be supplied to this controller (9) which outputs the output signal $CR^2_{measure}$ that is adapted to be supplied to a mixing point (1a) for modulating the input signal $CR^1_{ref}$ of the first control circuit (1).

5. An apparatus according to claim 1, wherein the second criterion comprises a lethal temperature KPT.

6. An apparatus according to claim 1, wherein the filled receptacles are bottles or cans.

7. An apparatus according to claim 1, wherein the second control circuit (2) includes a comparator which compares an input signal $CR^2_{ref}$ corresponding to a reference value of the second criterion and a further signal $CR^2_{measure}$ corresponding to an actual value of the second criterion, and which outputs an output signal corresponding to a control deviation resulting from the reference value/actual value comparison.

8. A method of pasteurizing filled receptacles, comprising:
controlling a first control circuit (1) according to a first criterion;
controlling at least one second control circuit (2) according to a second criterion, wherein the second control circuit (2) is superimposed on the first control circuit (1);
calculating an actual value of the first criterion based on a single and same process parameter with a unit (10) of the first control unit (1);
calculating an actual value of the second criterion based on the single and same process parameter with a unit (11) of the second control circuit (2);
supplying to a mixing point (1a) at which the second control circuit (2) is linked to an input signal $CR^1_{ref}$ of the first control circuit (1), wherein $CR^1_{ref}$ corresponds to a reference value of the first criterion and an output signal $CR^2_{set}$, of the second control circuit (2), wherein the output signal $CR^2_{set}$ modulates the input signal $CR^1_{ref}$ of the first control circuit (1) and wherein the mixing point (1a) is located in an input branch of the first control circuit (1);
controlling additional control circuits (3, ... N) according to further criteria supplying the output signals $CR^3_{set}$ ... $CR^N_{set}$ of the additional control circuits (3, ... N) to the mixing point (1a), wherein the output signals $CR^3_{set}$ ... $CR^N_{set}$ influence the input signal $CR^1_{ref}$ of the first control circuit (1); and
calculating actual values of the respective $3^{rd}$ to $N^{th}$ criteria based on the single and same process parameter with a unit of the respective control circuit (3, ... N),
wherein the first criterion comprises pasteurization units PU and the second criterion comprises a criterion different from the first criterion, and
wherein the single and same process parameter is a spray temperature $T^i_{spray}$, which transfers the pasteurization units PU to the filled receptacles.

9. A method according to claim 8, wherein the filled receptacles comprise at least one of bottles or cans.

* * * * *